(12) United States Patent
Black et al.

(10) Patent No.: US 9,655,659 B2
(45) Date of Patent: May 23, 2017

(54) ANCHOR TOWER

(71) Applicant: DeGen Medical, Inc., Florence, SC (US)

(72) Inventors: Craig Black, Florence, SC (US); Willie S. Edwards, Florence, SC (US); Rakesh P. Chokshi, Florence, SC (US); John E. Pendleton, Atlanta, GA (US); Ryan A. Lewis, Waxhaw, NC (US)

(73) Assignee: DeGen Medical, Inc., Florence, SC (US)

( * ) Notice: Subject to any disclaimer, the term of this patent is extended or adjusted under 35 U.S.C. 154(b) by 382 days.

(21) Appl. No.: 13/867,076

(22) Filed: Apr. 20, 2013

(65) Prior Publication Data
US 2014/0311264 A1 Oct. 23, 2014

(51) Int. Cl.
*A61B 17/70* (2006.01)

(52) U.S. Cl.
CPC ........ *A61B 17/7085* (2013.01); *A61B 17/708* (2013.01); *Y10T 74/18576* (2015.01)

(58) Field of Classification Search
CPC . A61B 17/7074–17/7086; A61B 17/70; F16H 25/12
USPC .......................................... 606/86 A, 99, 104
See application file for complete search history.

(56) References Cited

U.S. PATENT DOCUMENTS

| | | |
|---|---|---|
| 4,887,596 A | 12/1989 | Sherman |
| 5,817,094 A | 10/1998 | Errico et al. |
| 6,280,442 B1 | 8/2001 | Barker et al. |
| 6,530,929 B1 | 3/2003 | Justis et al. |
| 6,540,748 B2 | 4/2003 | Lombardo |
| 6,648,888 B1 * | 11/2003 | Shluzas ........................ 606/86 A |
| 7,008,422 B2 | 3/2006 | Foley et al. |
| 7,497,869 B2 | 3/2009 | Justis |
| 7,572,279 B2 | 8/2009 | Jackson |
| 6,530,929 C1 | 4/2010 | Justis et al. |
| 7,008,422 C1 | 4/2010 | Foley et al. |
| 7,717,944 B2 | 5/2010 | Foley et al. |
| 7,727,261 B2 | 6/2010 | Barker et al. |

(Continued)

FOREIGN PATENT DOCUMENTS

WO   WO0122893   4/2001

OTHER PUBLICATIONS

File history of U.S. Appl. No. 11/749,615, now U.S. Pat. No. 7,942,910, as of Nov. 27, 2013. Filing date, May 16, 2007. First Named Inventor, Robert L. Doubler. Title, Polyaxial Bone Screw.

(Continued)

*Primary Examiner* — Jacqueline Johanas
(74) *Attorney, Agent, or Firm* — Buchanan Nipper (57) ABSTRACT

Anchor towers useful in the alteration of a position of an item connected to an anchor are described. An anchor tower includes an inner sleeve and an outer sleeve disposed over and operably connected to the inner sleeve such that movement of the outer sleeve results in movement of the inner sleeve. A groove is disposed on the inner sleeve and an inwardly-extending projection is disposed on the outer sleeve. Relative movement between the inner and outer sleeves results in movement of the projection within the groove. This movement can produce desired movement of a portion of the inner sleeve, such as a distal arm, based on a structural configuration of the groove.

14 Claims, 6 Drawing Sheets

(56) References Cited

U.S. PATENT DOCUMENTS

| | | | |
|---|---|---|---|
| 7,749,232 B2 | 7/2010 | Salerni | |
| 7,763,055 B2 | 7/2010 | Foley | |
| 7,842,044 B2 * | 11/2010 | Runco et al. | 606/104 |
| 7,857,834 B2 | 12/2010 | Boschert | |
| 7,862,595 B2 | 1/2011 | Foley et al. | |
| 7,867,259 B2 | 1/2011 | Foley et al. | |
| 7,887,539 B2 | 2/2011 | Dunbar, Jr. et al. | |
| 7,892,238 B2 | 2/2011 | DiPoto et al. | |
| 7,918,878 B2 | 4/2011 | Songer et al. | |
| 7,922,727 B2 | 4/2011 | Songer et al. | |
| 7,942,909 B2 | 5/2011 | Hammill, Sr. et al. | |
| 7,942,910 B2 | 5/2011 | Doubler et al. | |
| 7,942,911 B2 | 5/2011 | Doubler et al. | |
| 7,947,065 B2 | 5/2011 | Hammill, Sr. et al. | |
| 7,951,173 B2 | 5/2011 | Hammill, Sr. et al. | |
| 8,002,806 B2 | 8/2011 | Justis | |
| 8,038,699 B2 | 10/2011 | Cohen et al. | |
| 8,075,603 B2 | 12/2011 | Hammill, Sr. et al. | |
| 8,092,460 B2 | 1/2012 | Geist et al. | |
| 8,105,362 B2 | 1/2012 | Duarte | |
| 8,123,751 B2 | 2/2012 | Shluzas | |
| 8,147,522 B2 | 4/2012 | Warnick | |
| 8,192,439 B2 | 6/2012 | Songer et al. | |
| 8,197,518 B2 | 6/2012 | Hammill, Sr. et al. | |
| 8,236,035 B1 | 8/2012 | Bedor | |
| 8,246,624 B2 | 8/2012 | Forton et al. | |
| 8,361,124 B2 | 1/2013 | Sherman et al. | |
| 8,460,308 B2 * | 6/2013 | Marino et al. | 606/104 |
| 8,845,649 B2 * | 9/2014 | Jackson | 606/99 |
| 8,894,662 B2 * | 11/2014 | Varieur et al. | 606/104 |
| 2002/0161368 A1 | 10/2002 | Foley et al. | |
| 2003/0060826 A1 | 3/2003 | Foley et al. | |
| 2005/0021031 A1 | 1/2005 | Foley et al. | |
| 2006/0079909 A1 * | 4/2006 | Runco et al. | 606/99 |
| 2006/0111714 A1 | 5/2006 | Foley | |
| 2008/0004625 A1 | 1/2008 | Runco et al. | |
| 2008/0045955 A1 * | 2/2008 | Berrevoets et al. | 606/61 |
| 2008/0125788 A1 | 5/2008 | Cohen et al. | |
| 2008/0269809 A1 | 10/2008 | Garamszegi | |
| 2008/0319477 A1 * | 12/2008 | Justis et al. | 606/232 |
| 2009/0082775 A1 | 3/2009 | Altarac et al. | |
| 2009/0171391 A1 | 7/2009 | Hutton et al. | |
| 2009/0171392 A1 | 7/2009 | Garcia-Bengochea et al. | |
| 2009/0326582 A1 | 12/2009 | Songer et al. | |
| 2009/0326586 A1 | 12/2009 | Duarte | |
| 2010/0137875 A1 * | 6/2010 | Marino et al. | 606/104 |
| 2010/0145389 A1 | 6/2010 | Triplett et al. | |
| 2010/0312279 A1 | 12/2010 | Gephart et al. | |
| 2011/0022088 A1 | 1/2011 | Forton et al. | |
| 2011/0040328 A1 | 2/2011 | Miller et al. | |
| 2011/0071571 A1 | 3/2011 | Abdelgany | |
| 2011/0093014 A1 | 4/2011 | Davis et al. | |
| 2011/0152942 A1 | 6/2011 | Oh et al. | |
| 2011/0257692 A1 * | 10/2011 | Sandstrom et al. | 606/86 A |
| 2011/0270325 A1 | 11/2011 | Keyer et al. | |
| 2012/0022597 A1 | 1/2012 | Gephart et al. | |
| 2012/0041490 A1 | 2/2012 | Jacob et al. | |
| 2012/0046700 A1 | 2/2012 | Jackson et al. | |
| 2012/0265212 A1 | 10/2012 | Seek | |
| 2012/0283786 A1 * | 11/2012 | Rezach et al. | 606/305 |
| 2012/0296380 A1 | 11/2012 | Simonson | |
| 2013/0261679 A1 * | 10/2013 | Mcbride et al. | 606/86 A |
| 2014/0052180 A1 * | 2/2014 | Justis et al. | 606/246 |
| 2014/0052197 A1 * | 2/2014 | Mcbride et al. | 606/86 A |
| 2014/0074106 A1 * | 3/2014 | Shin | 606/104 |
| 2014/0163625 A1 * | 6/2014 | Meyer et al. | 606/86 A |
| 2014/0277137 A1 * | 9/2014 | Stad et al. | 606/246 |
| 2014/0277206 A1 * | 9/2014 | Reitblat et al. | 606/86 A |
| 2014/0316475 A1 * | 10/2014 | Parikh et al. | 606/86 A |

OTHER PUBLICATIONS

File history of U.S. Appl. No. 12/355,145, now U.S. Pat. No. 7,947,065, as of Nov. 27, 2013. Filing date, Jan. 16, 2009. First Named Inventor, John E. Hammill. Title, Locking Polyaxial Ball and Socket Fastener.

File history of U.S. Appl. No. 12/700,436, now U.S. Pat. No. 7,951,173, as of Nov. 27, 2013. Filing date, Feb. 4, 2010. First Named Inventor, John E. Hammill. Title, Pedicle Screw Implant System.

File history of U.S. Appl. No. 12/833,751, now U.S. Pat. No. 8,075,603, as of Nov. 27, 2013. Filing date, Jul. 9, 2010. First Named Inventor, John E. Hammill. Title, Locking Polyaxial Ball and Socket Fastener.

File history of U.S. Appl. No. 13/317,969, as of Nov. 27, 2013. Filing date, Nov. 1, 2011. First Named Inventor, Roger P. Jackson. Title, Polyaxial Bone Anchor With Pop-on Shank and Pivotable Retainer.

\* cited by examiner

ANCHOR TOWER

DESCRIPTION OF EMBODIMENTS

The following detailed description and the appended drawings describe and illustrate various example embodiments. The description and illustration of these examples are provided to enable one skilled in the art to make and use an anchor tower. They are not intended to limit the scope of the claims in any manner.

As used herein, the term "groove" refers to an indentation in a surface having a length that is greater than a width. The term does not require any particular cross-sectional shape of the indentation with respect to a lengthwise axis of the groove or a portion of the groove, and encompasses all cross-sectional shapes that can be used within the scope of this definition. Non-limiting examples of cross-sectional shapes that can be used for the grooves in the anchor towers include a u-shape, a v-shape, a semi-circular shape, and an arcuate shape. The term does not require any particular lengthwise configuration, either. Non-limiting examples of lengthwise configurations that can be used for the grooves in the anchor towers include linear, curvilinear, segmented linear, and tortuous paths.

Figure 1:
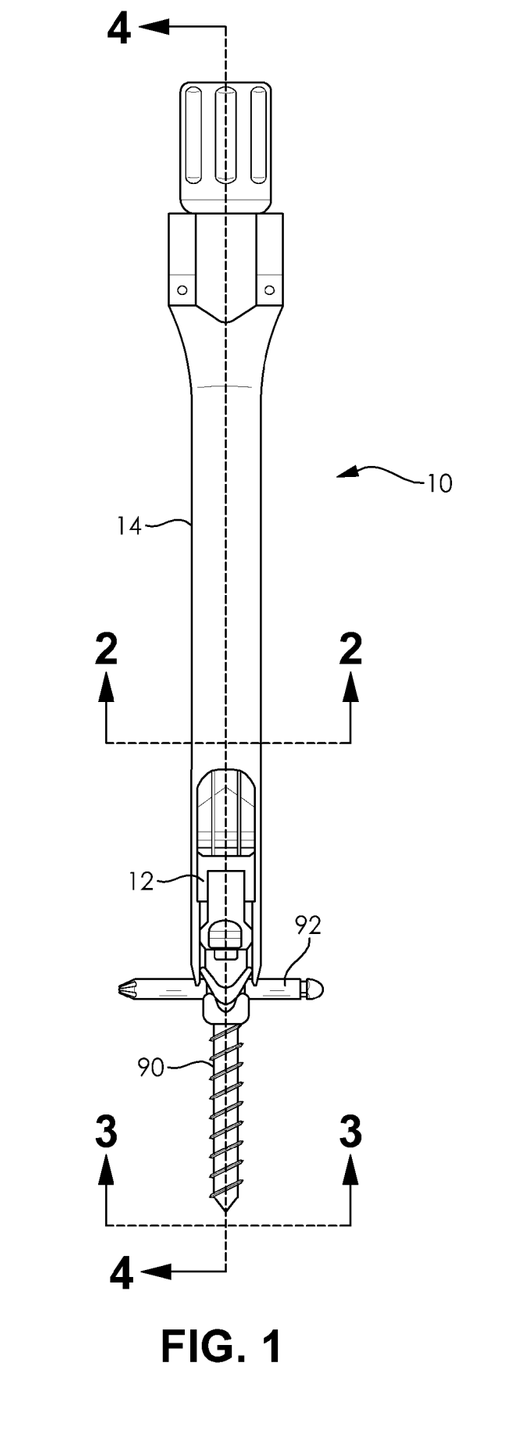
FIG. 1 illustrates an embodiment of an anchor tower. The anchor tower is illustrated with an engaged anchor and rod.
Figure 2:
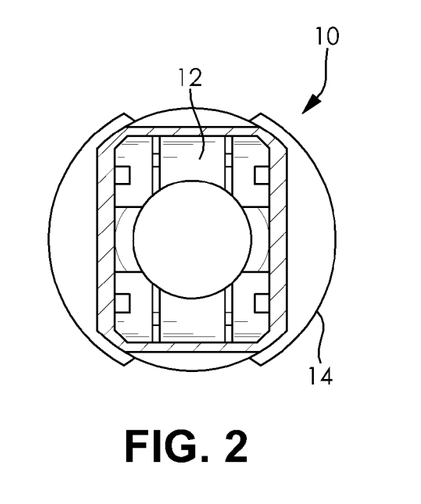
FIG. 2 is a sectional view of the anchor tower illustrated in FIG. 1, taken along line 2-2.
Figure 3:
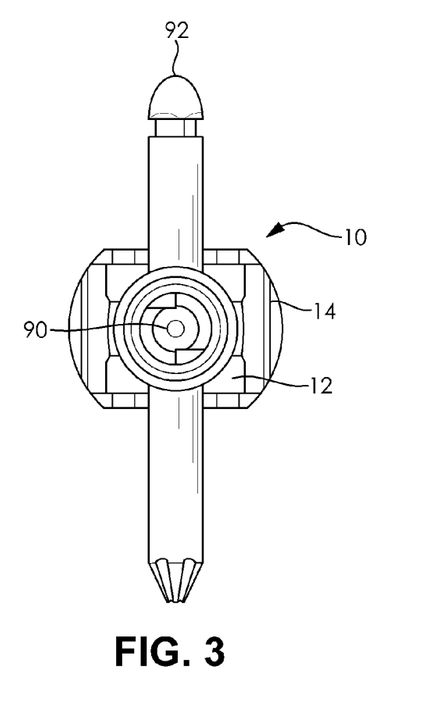
FIG. 3 is a sectional view of the anchor tower illustrated in FIG. 1, taken along line 3-3.
Figure 4:
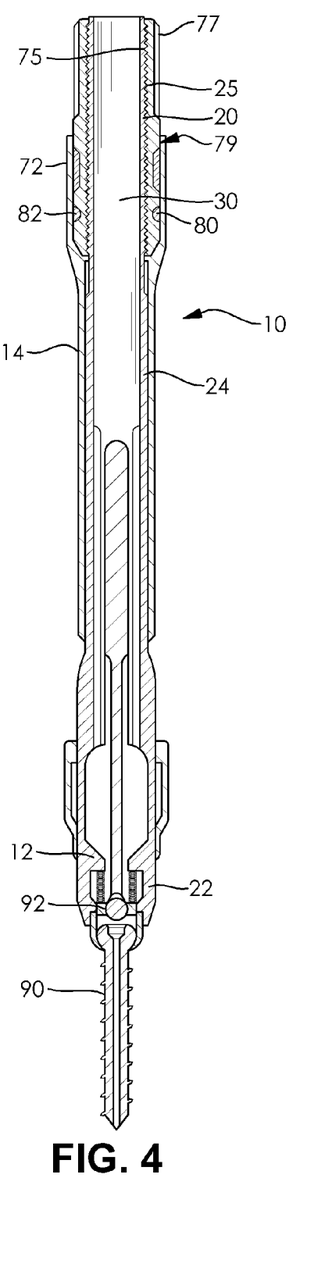
FIG. 4 is a sectional view of the anchor tower illustrated in FIG. 1, taken along line 4-4.

In FIGS. 1, 2, 3, 4, 5, 6A, 6B, 8A and 8B, an anchor tower 10 comprises an inner sleeve 12 and an outer sleeve 14 disposed over and operably connected to the inner sleeve 10 such that movement of the outer sleeve 14 results in movement of the inner sleeve 12, such as in the manner described below. In FIGS. 1, 3, and 4, the anchor tower 10 is illustrated with an engaged anchor 90 and rod 92, each of which is separable from the anchor tower 10.

The inner sleeve 12 has a proximal end 20, a distal end 22, a cylindrical portion 24, and first 26 and second 28 arms that extend from the cylindrical portion to the distal end 22. Thread 25 is disposed on the proximal end 20 of the inner sleeve 12. Thread 25 can be defined by an outer surface of the inner sleeve 12, such as illustrated in FIG. 4, or can be formed by another component disposed on the inner sleeve 12. A central passageway 30 extends through the cylindrical portion 24. A slot 32 separates the first 26 and second 28 arms. The first arm 26 includes an intermediate longitudinal portion 34 that has a reduced radial thickness as compared to a radial thickness of a proximal longitudinal portion 36. Similarly, the second arm 28 includes an intermediate longitudinal portion 38 that has a reduced radial thickness as compared to a radial thickness of a proximal longitudinal portion 40. The first arm 26 includes a distal longitudinal portion 42 that defines a first ramped inward projection 44 and the second arm 28 includes a distal longitudinal portion 46 that defines a second ramped inward projection 48. The first 44 and second 48 ramped inward projections cooperatively define a throat 50 that opens to the distal end 22 of the inner sleeve 12 and into the slot 32 that separates the first 26 and second 28 arms.

Figures 5, 6A, 6B:
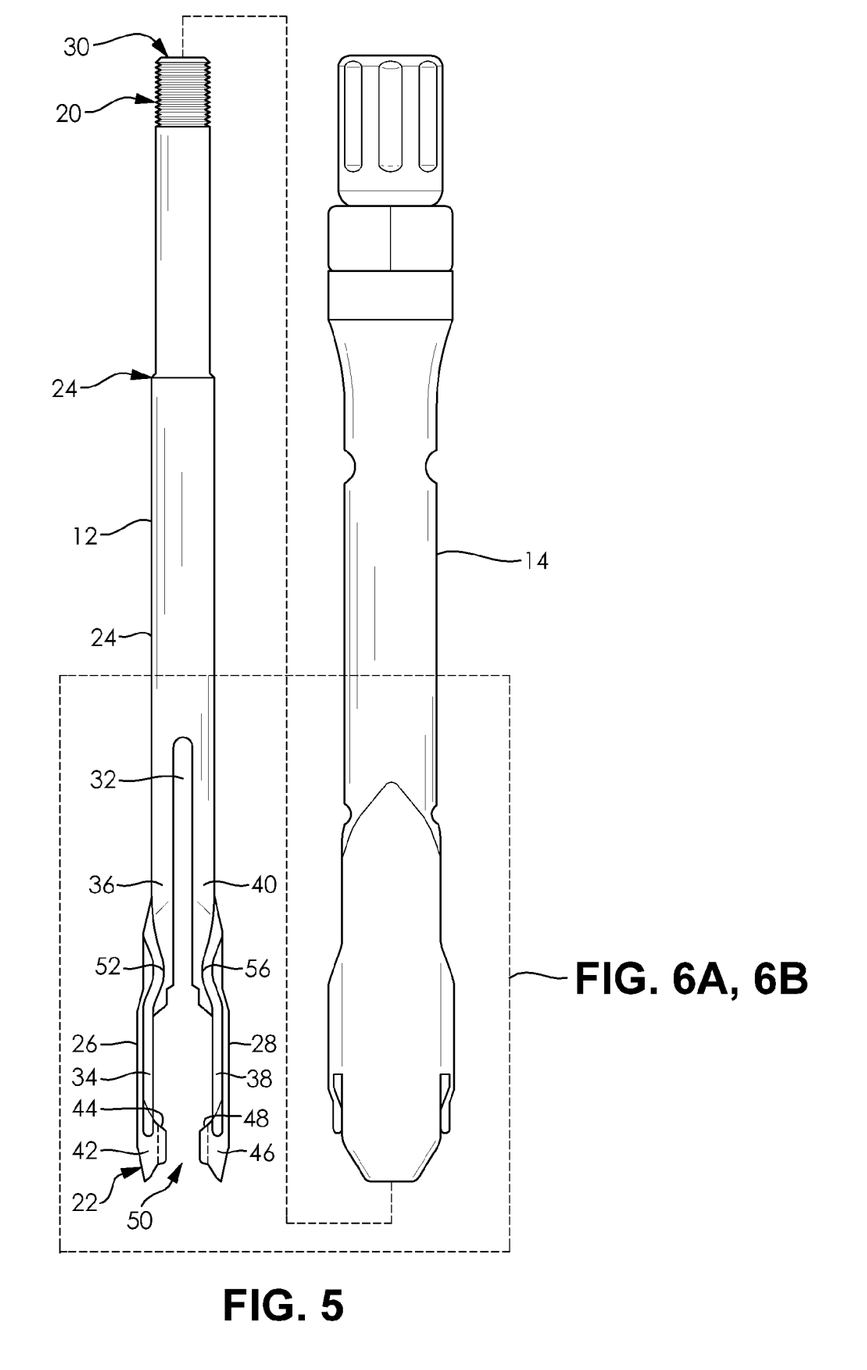
FIG. 5 is an exploded diagram of the anchor tower illustrated in FIG. 1.
FIG. 6A is a magnified view of the distal end of the inner sleeve component of the anchor tower illustrated in FIG. 1.
FIG. 6B is a magnified view of the distal end of the outer sleeve component of the anchor tower illustrated in FIG. 1.
Figure 6A:
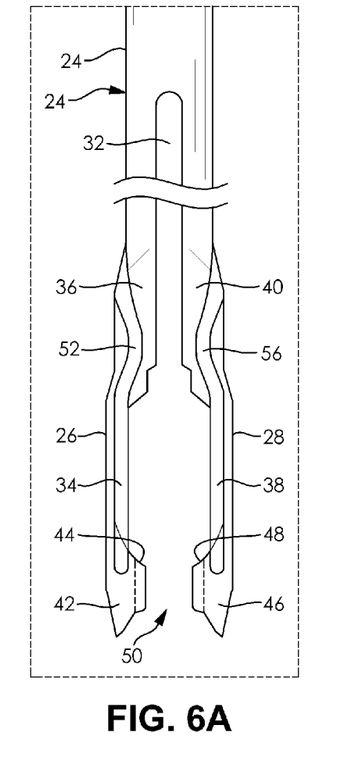
Figure 6B:
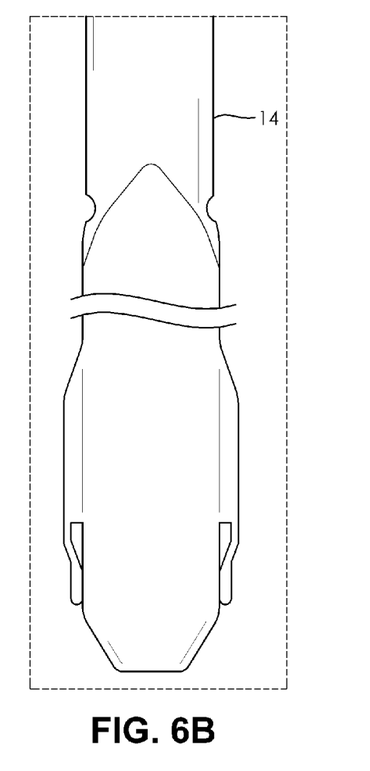
Figure 7:
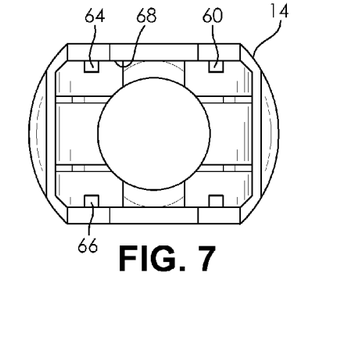
FIG. 7 is an end view of the outer sleeve component of the anchor tower illustrated in FIG. 1.
Figure 7A:
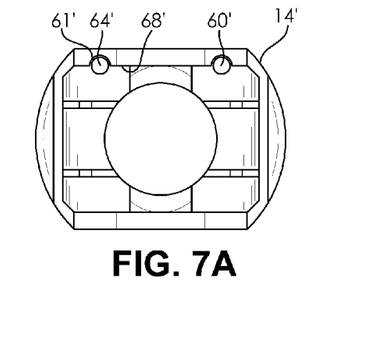
FIG. 7A is an end view of an alternative outer sleeve component.

The first arm 26 defines a first groove 52 that extends along a portion of the first arm 26. As best illustrated in FIG. 6A, the first groove 52 has a tortuous path configuration as it extends along the proximal longitudinal portion 36 of the first arm 26, a linear configuration as it extends along the intermediate longitudinal portion 34 of the first arm 26, and a linear configuration as it extends along the distal longitudinal portion 42 of the first arm 26. This arrangement provides various stop points, due to interference fits, as the outer sleeve 14 is moved along the inner sleeve 12, as described below. It is noted, however, that the first groove 52 can have any configuration as it extends along each of the proximal 36, intermediate 34 and distal 42 longitudinal portions of the first arm 26. As best illustrated in FIG. 7A, the first groove 52 can have an s-shaped configuration as it extends along the proximal longitudinal portion 36 of the first arm 26.

Also as best illustrated in FIG. 6A, first groove 52 has a flared opening in the proximal longitudinal portion 36 and a closed end in the distal longitudinal portion 42. The flared opening provides the opening with a cross-sectional width that is greater than a cross-sectional width at another position along the length of the first groove 52. This structure provides play in the interaction of the appropriate projection of the outer sleeve 14, as described below, as the projection enters the first groove 52. The opening of the first groove 52 can have any configuration, though, and the flared opening is optional. For example, the opening can have the same cross-sectional width as another position along the length of the first groove 52. Also, the first groove 52 can have a constant cross-sectional width along its entire length.

Also as best illustrated in FIG. 6A, a portion of the first groove 52 is open as it extends the proximal longitudinal portion 36 and the intermediate longitudinal portion 34. That is, the portions of the first groove 52 are recessed into more than a single surface of the first arm 26 in these portions of the first arm 26. Other portions of the first groove 26 are closed, i.e., recessed into only a single surface of the first arm.

Also as best illustrated in FIG. 6A, the first groove 52 extends along the entire axial length of the proximal longitudinal portion 36 and the intermediate longitudinal portion 34, but only along a portion of the axial length of the distal longitudinal portion 46. This provides an absolute stop to the movement of the outer sleeve 14 along the inner sleeve 12, as described below.

In one embodiment, the first arm 26 also defines a second groove (not visible in the Figures) on the opposite side of the first arm 26 from the first groove 52. If included, the second groove can have the same configuration as the first groove 52. It is noted, however, that the second groove can have any configuration, including a configuration that is different from that of the first groove 52. Inclusion of this second groove on the first arm 26 is optional.

The second arm 28 defines a third groove 56 that extends along a portion of the second arm 28. As best illustrated in FIG. 6A, the third groove 56 in the illustrated embodiment is a mirror image of the first groove 52 with respect to a longitudinal axis of the inner sleeve 12. Thus, the third groove 56 has a tortuous path configuration as it extends along the proximal longitudinal portion 40 of the second arm 28, a linear configuration as it extends along the intermediate longitudinal portion 38 of the second arm 28, and a linear configuration as it extends along the distal longitudinal portion 46 of the second arm 28. As with the first groove 52 on the first arm 26, this arrangement provides various stop points, due to interference fits, as the outer sleeve 14 is moved along the inner sleeve 12, as described below. It is noted, however, that the third groove 56 can have any configuration as it extends along each of the proximal 40, intermediate 38 and distal 46 longitudinal portions of the second arm 26, including a configuration that is different from that of the first groove 52 on the first arm 26, a configuration that is identical to that of the first groove 52 on the first arm 26, and, as illustrated in FIG. 6A, a mirror image of the configuration of the first groove 52 on the first arm 26 with respect to a longitudinal axis of the inner sleeve 12. As best illustrated in FIG. 6A, the third groove 56 can have an s-shaped configuration as it extends along the proximal longitudinal portion 40 of the second arm 28. Inclusion of the third groove 56 on the second arm 28 is optional.

Similar to the first arm 26, the second arm 28 can define another groove (not illustrated in the Figures) on the opposite side of the second arm 28 from the third groove 56. If included, this additional groove can have the same configuration as the third groove 56, or a configuration that is different from that of the third groove 56. Inclusion of this additional groove on the second arm 28 is optional.

Figure 8A:
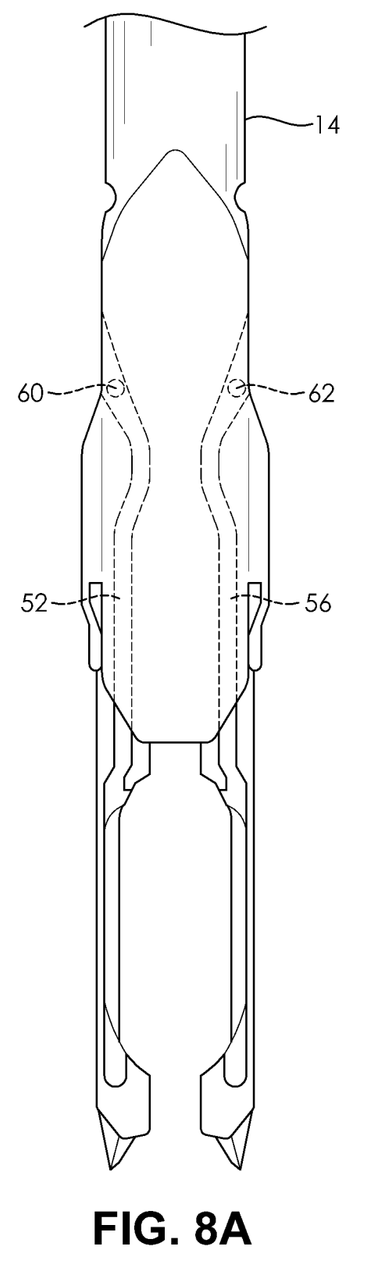
FIG. 8A is a magnified view of the distal end of the anchor tower in a first configuration.

As best illustrated in FIG. 8, the distal end 70 of the outer sleeve 14 defines first 60, second 62, third 64, and fourth 66 projections that extend from an inner surface 68 of the outer sleeve 14. Each of the projections 60, 62, 64, 66 is adapted to be movable along and partially within one of the grooves defined by the inner sleeve 12. As such, each of the projections 60, 62, 64, 66 can have any suitable size and configuration that allows the projection to be positioned within and movable along a portion of one of the grooves. In the illustrated embodiment, each of the projections 60, 62, 64, 66 comprises a cylindrical-shaped projection having a cross-sectional diameter that is less than a width of a portion of a groove defined by the inner sleeve 12. Non-limiting examples of other suitable configurations for the projections 60, 62, 64, 66 include a hemispherical projection, a projection having a square cross-sectional shape and a projection having rectangular cross-sectional shape.

In the illustrated embodiment, each of the projections 60, 62, 64, 66 is continuously formed with the outer sleeve 14. It is noted, though, that one or more of the projections can comprise a separately attached member, such as a solid projection adhered to or otherwise attached, permanently or temporarily, to the inner surface of the outer sleeve 14. Also, other structures can be used for one or more projections in a particular embodiment. For example, as illustrated in FIG. 7A, a ball bearing, such as captive ball bearings 60', 64', can be used as a projection in conjunction with a recess, such as recess 61', defined by the outer sleeve 14'. In the embodiment illustrated in FIG. 7A, the outer sleeve 14' includes an inner surface 68' and two captive bearings 60', 64' disposed on the same side of the outer sleeve 14'. The projections could be disposed on opposite sides of the outer sleeve 14'.

While the illustrated embodiment includes four projections, any number of projections can be included in an anchor tower according to a particular embodiment. In some embodiments, a number of projections is equal to a number of grooves defined by the inner sleeve of the anchor tower is used. In other embodiments, a number of projections that is less than a number of grooves defined by the inner sleeve of the anchor tower is used.

Thread 75 is disposed on the proximal end 72 of the outer sleeve 14. As best illustrated in FIG. 4, thread 75 can be formed on an inner surface of an actuator 77 that is rotatably disposed within a chamber 79 formed in the proximal end of the outer sleeve 14. A ridge 80 on the inner surface of the outer sleeve 14 is received by a mating groove 82 defined by the actuator 77 such that the actuator 77 is connected to and a component of the outer sleeve 14 that can be rotated within and independent of the remainder of the outer sleeve 14. The ridge 80 and groove 82 can be circumferential or partial circumferential in nature. Thread 75 mates with thread 25 of the inner sleeve 12 to form an operable connection between the outer sleeve 14 and the inner sleeve 12 such that rotation of the actuator 77, which moves independently of the remainder of the outer sleeve 14, about a longitudinal axis of the anchor tower 10 results in axial movement of the inner sleeve 14 along the longitudinal axis.

Other structures can be used to achieve the desired relative movement between the outer and inner sleeves of an anchor tower according to a particular embodiment. For example, the outer sleeve can define an inner passageway that slidably accepts the inner sleeve. In these embodiments, a user simply advances the outer sleeve along the lengthwise axis The anchor tower 10 is useful for extending an anchor, such as a screw or other fastener. It can be used to extend an anchor in a manner that cooperates with the anchor to form a passageway adapted to guide the loading of an element into a recess defined by the anchor. The anchor tower 10 can be used in a variety of situations and contexts. For example, the anchor tower 10 can be used with bone anchors, such as pedicle screws, to extend the bone anchors during a treatment procedure in a manner that forms an opening adapted to guide the loading of a rod, such as a spinal rod, into a recess defined by the head of the bone anchor. As such, the anchor tower 10 is useful in surgical and minimally invasive spinal treatment procedures.

All components of the anchor tower can be made from any suitable material. Non-limiting examples of suitable materials include metals, such as stainless steel and other metals, and plastics commonly used in medical devices.

In use, the outer sleeve 14 is disposed over the inner sleeve 12. The outer sleeve is operably connected to the inner sleeve 12 by a mating thread connection between threads 25 and 75, as best illustrated in FIG. 4. Rotation of the proximal end of the outer sleeve 14, such as the actuator 77 of the illustrated embodiment, about a longitudinal axis of the anchor tower 10 results in axial movement of inner sleeve 12 along the longitudinal axis. During such movement, when the inner sleeve 12 has moved axially by a sufficient amount, the projections 60, 62, 64, 66 of the outer sleeve 14 enter the corresponding grooves 52, 56 of the inner sleeve 12. For the illustrated embodiment, the tortuous path defined by the portions of the grooves 52, 56 that extend along the corresponding proximal longitudinal portions 36, 40 of the first 26 and second 28 arms provides various stops to militate against continued relative axial movement between the outer sleeve 14 and the inner sleeve 12. These stops are overcome, however, with continued movement of the outer sleeve 14, such as continued rotational movement of the actuator 77. Thus, the structures of the inner 12 and outer 14 sleeves cooperate to provide feedback to the user related to the current configuration of the anchor tower 10.

Figure 8B:
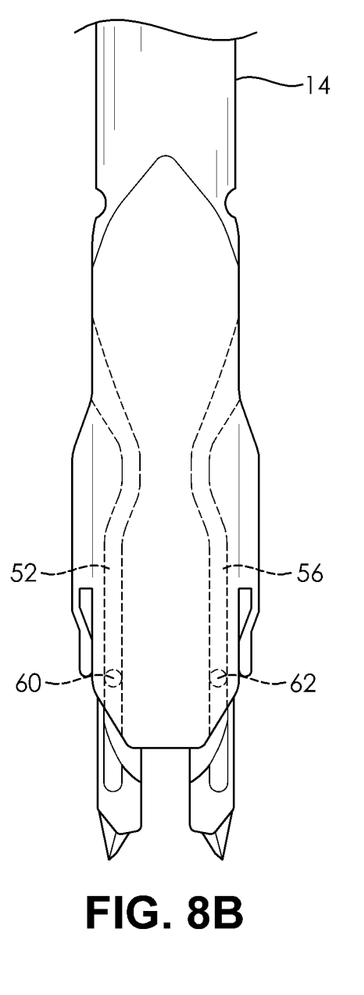
FIG. 8B is a magnified view of the distal end of the anchor tower in a second configuration.

FIGS. 8A and 8B illustrate the anchor tower 10 in two different configurations. In FIG. 8A, the anchor tower 10 is in a first configuration in which the outer sleeve 14 is positioned with the projections 60, 62 disposed in the portion of the respective groove 52, 56 that extends along the respective proximal longitudinal portion 36, 40 of the respective arm 26, 28 of the inner sleeve 12. In FIG. 8B, the anchor tower 10 is in a second configuration in which the outer sleeve 14 is positioned with the projections 60, 62 disposed in the portion of the respective groove 52, 56 that extends along the respective intermediate longitudinal portion 34, 38 of the respective arm 26, 28 of the inner sleeve 12. To move the anchor tower 10 from the first configuration to the second configuration, a user rotates the proximal end of the outer sleeve 14, such as the actuator 77 in the illustrated embodiment, about a longitudinal axis of the anchor tower 10 to cause axial movement of inner sleeve 12 along the longitudinal axis. The user continues to rotate the proximal end of the outer sleeve 14 until a desired degree of relative movement between the outer 14 and inner 12 sleeves has occurred. Reverse rotational movement of the proximal end of the outer sleeve can be applied to cause axial movement of the inner sleeve along the longitudinal axis of the anchor tower in an opposite direction.

Figure 9A:
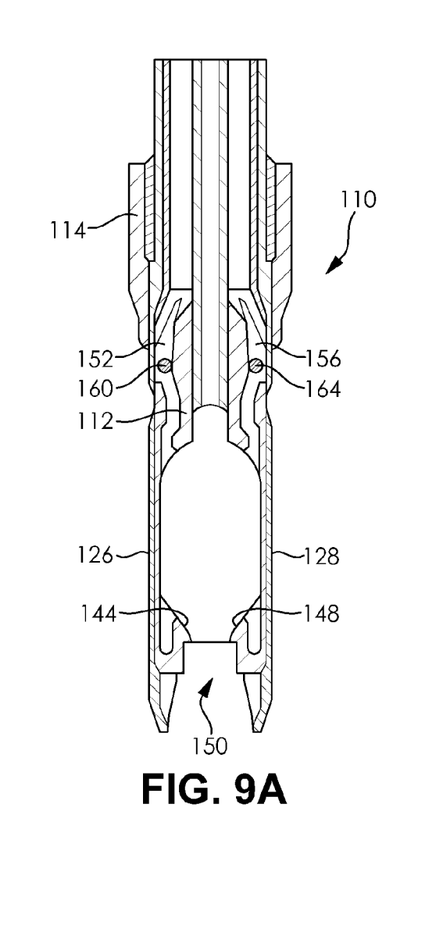
FIG. 9A is a sectional view of the distal end of another embodiment of an anchor tower, shown in one configuration.
Figure 9B:
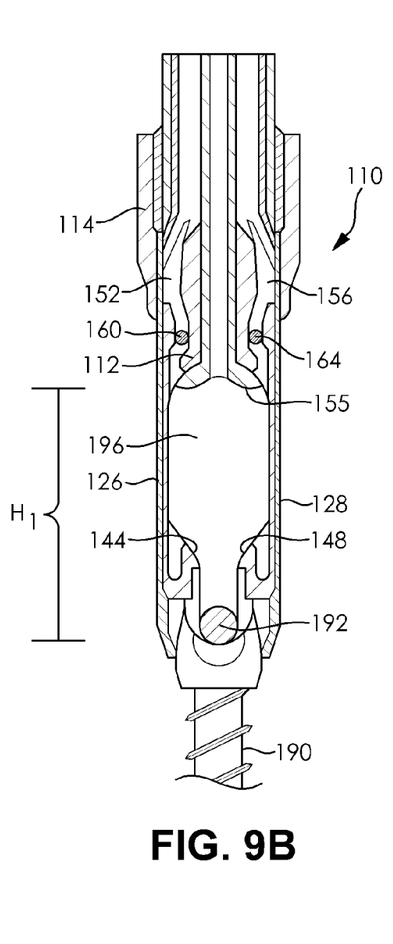
FIG. 9B is a sectional view of the distal end of the anchor tower illustrated in FIG. 9A, shown in another configuration. The anchor tower is illustrated with an engaged anchor and rod
Figure 9C:
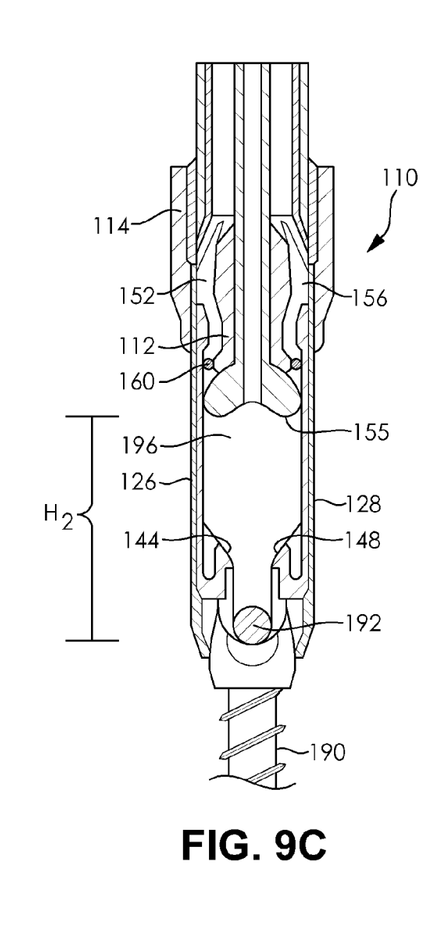
FIG. 9C is a sectional view of the distal end of the anchor tower illustrated in FIGS. 9A and 9B, shown in another configuration. The anchor tower is illustrated with an engaged anchor and rod

FIGS. 9A, 9B, and 9C illustrate the distal end of another anchor tower 110 in various configurations during use. In FIGS. 9B and 9C, the anchor tower 110 is illustrated with an engaged anchor 190 and rod 192.

Anchor tower 110 is similar to the anchor tower 10 described above and illustrated in FIGS. 1, 2, 3, 4, 5, 6A, 6B, 8A and 8B, except as described below. Thus, anchor tower 110 comprises an inner sleeve 112 and an outer sleeve 114 disposed over and operably connected to the inner sleeve 110. Projections 160, 164 are defined by the outer sleeve 114 and are movable within first 152 and second 156 grooves defined by the inner sleeve 112. Each of the grooves 152, 156 in this embodiment defines a segmented path defined by a series of angulated surfaces. During relative movement between the outer 114 and inner 112 sleeves, interaction between the projections 160, 164 of the outer sleeve with the angulated surfaces of the inner sleeve 112 that define the grooves 152, 156 causes lateral distal portions, such as arms 126, 128, of the inner sleeve 112 to move in radially outward and inward directions, depending on the particular angulated surface interacting with the projections 160, 164. This controlled radial movement of portions of the inner sleeve 112 can be used to engage and/or disengage items being used with the anchor tower, such as anchor 190.

In FIG. 9A, the anchor tower 110 is in a first configuration. In this configuration, the arms 126, 128 are separated by the throat 150 and the anchor tower 110 is free of any other items. In FIG. 9B, the anchor tower 110 is in a second configuration in which the anchor tower 110 is engaged with anchor 190 to form opening 196. Rod 192 has been disposed across an upper channel of the anchor, guided by the ramped surfaces 144, 148 of the inner sleeve 112. In this configuration, opening has a first height $H_1$. In FIG. 9C, the anchor tower 110 is in a third configuration in which the continued relative movement between the inner 112 and outer 114 sleeves has reduced the height of the opening 196. Thus, in this configuration, opening 196 has a second height $H_2$ that is less than the first height $H_1$ illustrated in FIG. 9B. In this configuration, the continued relative movement between the inner 112 and outer 114 sleeves has reduced the height of the opening 196, effectively bringing the anchor 190 closer to the distal end of the outer sleeve 114. Moving the anchor tower 110 from the second configuration to the third configuration can be useful in the alteration of a position of an item connection to the anchor 190, such as a vertebra or other bone. The anchor tower 110 is movable between these configurations by causing the relative movement between the outer 114 and inner sleeves 112 as appropriate for the particular structure of the outer sleeve 114, such as the rotational or axial movement described above. Rod 192 can be used to span and connect multiple anchors, effectively connecting the items connected to the anchors, such as two or more vertebrae. Using an appropriate number of anchor towers 110 in conjunction with an appropriate number of anchors and a rod allows a user to manipulate the relative positioning of the items connected to the anchors, such as two or more vertebrae.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

We claim:

1. An anchor tower, comprising:
   an inner sleeve having a first outer surface, a first lateral surface that is different than the first outer surface, a first proximal end and a first distal end, an outer thread disposed on the first proximal end, and the first outer surface defining a groove on the first distal end having a proximal portion and a distal portion, the first outer surface defining a first lateral opening in communication with the groove and open to the first lateral surface, the first lateral opening being a flared opening in the proximal portion, the groove having a closed distal end in the distal portion, the groove comprising a tortuous path;
   an outer sleeve disposed over the inner sleeve and having an inner surface, a second proximal end and a second distal end, the second proximal end defining a chamber and the inner surface defining an inwardly-extending projection;
   an actuator disposed within the chamber and defining an inner thread mated with the outer thread, the actuator rotatable within the chamber about a lengthwise axis of said anchor tower;
   wherein the inner sleeve moves axially along the lengthwise axis in response to rotational movement of the actuator such that the inwardly-extending projection moves within the groove; and
   wherein the flared opening provides play in the interaction with the inwardly-extending projection as the inwardly-extending projection enters the groove.

2. The anchor tower of claim 1, wherein the inner sleeve has a body portion and first and second arms extending away from the body portion; and wherein the groove is disposed on the first arm.

3. The anchor tower of claim 2, wherein the body portion comprises a cylindrical portion.

4. The anchor tower of claim 2, wherein the first arm is positioned opposite the second arm with respect to the lengthwise axis.

5. The anchor tower of claim 4, wherein the first outer surface defines a second groove on the first distal end.

6. The anchor tower of claim 5, wherein the second groove is disposed on the second arm.

7. The anchor tower of claim 6, wherein the second groove has a configuration that is a mirror image of the configuration of the first groove.

8. The anchor tower of claim 5, wherein the inner surface defines a second inwardly-extending projection that is movable within the second groove.

9. The anchor tower of claim 1, wherein a portion of the groove is recessed into more than a single surface of the inner sleeve.

10. The anchor tower of claim 1, wherein the inner sleeve has a body portion, first and second arms extending away from the body portion, and a slot separating the first and second arms, the slot extending from the first distal end proximally beyond the first lateral opening;

wherein the groove is disposed on the first arm.

11. An anchor tower, comprising:
an inner sleeve having a first outer surface, a first lateral surface that is different than the first outer surface, a first proximal end and a first distal end, an outer thread disposed on the first proximal end and the first outer surface defining first and second grooves on the first distal end, the first outer surface defining a first lateral opening in communication with the first groove and a second lateral opening in communication with the second groove, the first groove having a first proximal portion and a first distal portion, the first lateral opening open to the first lateral surface and being a first flared opening in the first proximal portion, the first groove having a first closed distal end in the first distal portion and comprising a tortuous path, the second groove having a second proximal portion and a second distal portion, the second lateral opening being a second flared opening in the second proximal portion, the second groove having a second closed distal end in the second distal portion and comprising a tortuous path;
an outer sleeve disposed over the inner sleeve and having an inner surface, a second proximal end and a second distal end, the second proximal end defining a chamber and the inner surface defining first and second inwardly-extending projections;
an actuator disposed within the chamber and defining an inner thread mated with the outer thread, the actuator rotatable within the chamber about a lengthwise axis of said anchor tower;
wherein the inner sleeve moves axially along the lengthwise axis in response to rotational movement of the actuator such that the first inwardly-extending projection moves within the first groove and the second inwardly-extending projection moves within the second groove;
wherein the first flared opening provides play in the interaction with the first inwardly-extending projection as the first inwardly-extending projection enters the first groove; and
wherein the second flared opening provides play in the interaction with the second inwardly-extending projection as the second inwardly-extending projection enters the second groove.

12. The anchor tower of claim 11, wherein the inner sleeve has a body portion and first and second arms extending away from the body portion;

wherein the first groove is disposed on the first arm; and
wherein the second groove is disposed on the second arm.

13. The anchor tower of claim 11, wherein the second groove has a configuration that is a mirror image of the configuration of the first groove.

14. An anchor tower, comprising:
an inner sleeve having a first outer surface, a first lateral surface that is different than the first outer surface, a first proximal end and a first distal end, an outer thread disposed on the first proximal end and the outer surface defining a plurality of grooves on the first distal end and a first lateral opening, a first pair of the plurality of grooves having a first configuration and a second pair of the plurality of grooves having a second configuration, the first pair of the plurality of grooves comprising a first groove and a second groove and the second pair of the plurality of grooves comprising a third groove and a fourth groove, each of the first, second, third, and fourth grooves having a proximal portion and a distal portion, a flared opening in the proximal portion, and a closed distal end in the distal portion, each of the first, second, third, and fourth grooves comprising a tortuous path, the first lateral opening in communication with the first groove, open to the first lateral surface, and comprising the flared opening in the proximal portion of the first groove;
an outer sleeve disposed over the inner sleeve and having an inner surface, a second proximal end and a second distal end, the second proximal end defining a chamber and a plurality of inwardly-extending projections disposed on the inner surface;
an actuator disposed within the chamber and defining an inner thread mated with the outer thread, the actuator rotatable within the chamber about a lengthwise axis of said anchor tower;
wherein the inner sleeve moves axially along the lengthwise axis in response to rotational movement of the actuator such that one of the plurality of inwardly-extending projections moves within one of the pluralities of grooves; and
wherein the flared opening of each of the first, second, third, and fourth grooves provides play in the interaction with one of the inwardly-extending projections of the plurality of inwardly-extending projections as the one of the inwardly-extending projections enters one of the first, second, third, and fourth grooves having the flared opening.

* * * * *